(12) United States Patent
Elkins

(10) Patent No.: US 6,551,347 B1
(45) Date of Patent: *Apr. 22, 2003

(54) COOLING/HEATING SYSTEM

(75) Inventor: William Elkins, San Jose, CA (US)

(73) Assignee: Life Enhancement Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/022,822

(22) Filed: Feb. 24, 1993

Related U.S. Application Data

(60) Continuation of application No. 07/899,220, filed on Jun. 16, 1992, now abandoned, which is a continuation of application No. 07/733,453, filed on Jul. 22, 1991, now abandoned, which is a continuation-in-part of application No. 07/431,753, filed on Nov. 6, 1989, now Pat. No. 5,033,136, which is a division of application No. 07/250,778, filed on Sep. 28, 1988, now Pat. No. 4,884,304.

(51) Int. Cl.$^7$ .................................................. A61F 7/00
(52) U.S. Cl. ........................................ 607/104; 165/46
(58) Field of Search ................. 165/46; 607/104–114; 62/259.3

(56) References Cited

U.S. PATENT DOCUMENTS

| | | | | |
|---|---|---|---|---|
| 3,007,473 A | * | 11/1961 | Jackson et al. ............. | 128/400 |
| 3,233,662 A | * | 2/1966 | Yuen ......................... | 128/403 |
| 3,295,594 A | * | 1/1967 | Hopper ....................... | 165/46 |
| 3,490,523 A | * | 1/1970 | Esmond ....................... | 165/46 |
| 3,830,676 A | * | 8/1974 | Elkins ........................ | 128/413 |
| 4,149,541 A | * | 4/1979 | Gammons et al. .......... | 128/400 |
| 4,335,726 A | * | 6/1982 | Kolstedt ..................... | 128/400 |
| 4,691,762 A | * | 9/1987 | Elkins et al. ............... | 128/400 |
| 4,846,176 A | * | 7/1989 | Golden ....................... | 128/379 |

FOREIGN PATENT DOCUMENTS

| | | | | |
|---|---|---|---|---|
| WO | 8503216 | * | 8/1985 | ................. 128/400 |

* cited by examiner

*Primary Examiner*—Mark S. Graham

(57) ABSTRACT

Equipment for thermal therapy of patients is disclosed. The equipment includes a flexible heat exchange structure having fluid conducting channels formed between two layers of flexible material, with improved liquid manifolds at the ends of the channels for resisting pinching, crimping or buckling in the manifolds on pressurization and when the heat exchange structure is subjected to flexure as when worn on the human body. The manifolds are configured so that pressurization shrinkage at the manifold is balanced with pressurization shrinkage laterally among the fluid conducting channels. In a preferred embodiment, the fluid conducting channels themselves are configured in a zig-zag pattern which is effective to resist buckling or pinching of the channels when the heat exchange structure is subjected to bending. In a further embodiment the flexible heat exchange structure includes a third layer of material to form a pressurized air envelope, for heat/cold and pressure therapy.

20 Claims, 6 Drawing Sheets

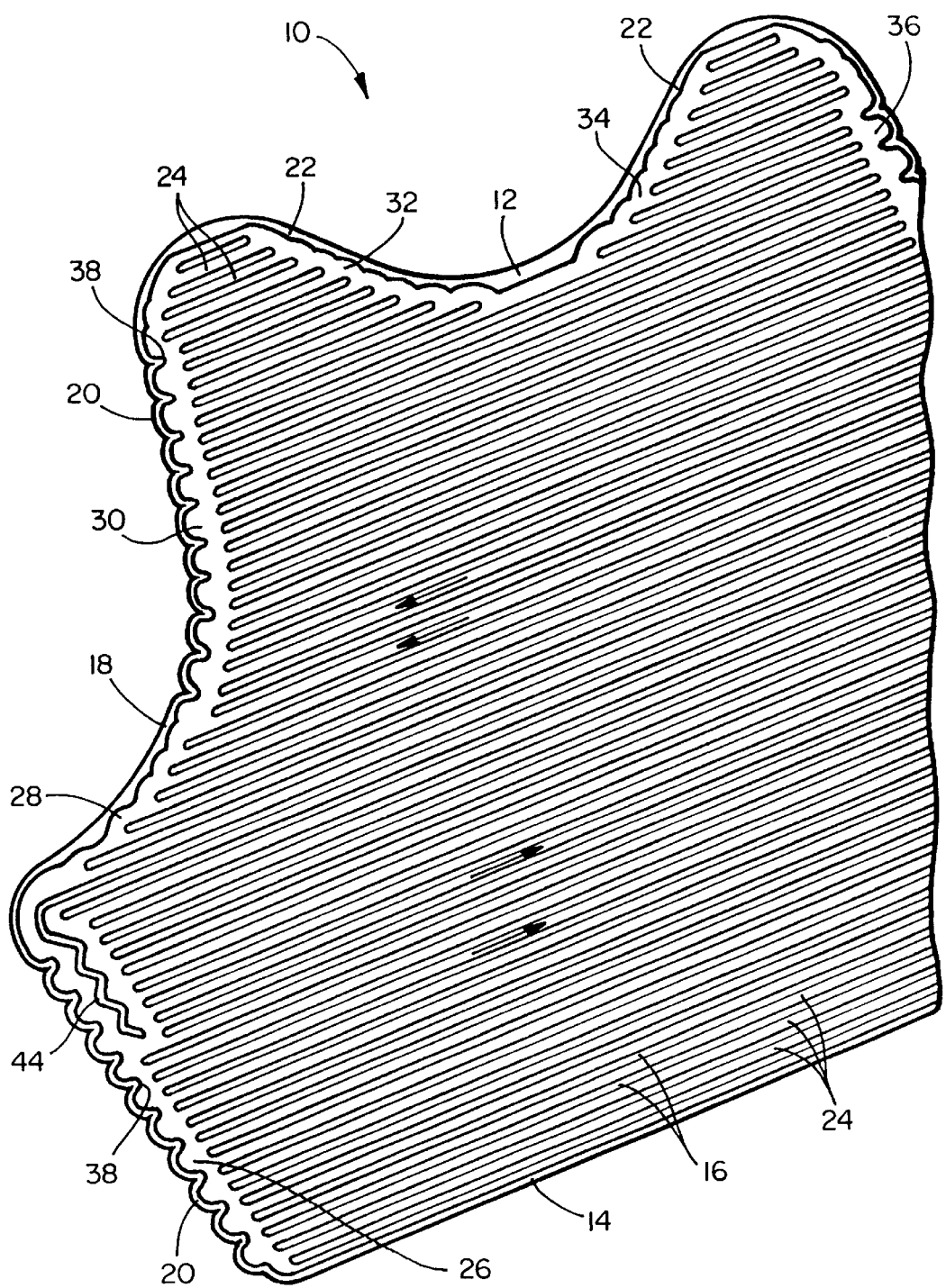
FIG_1

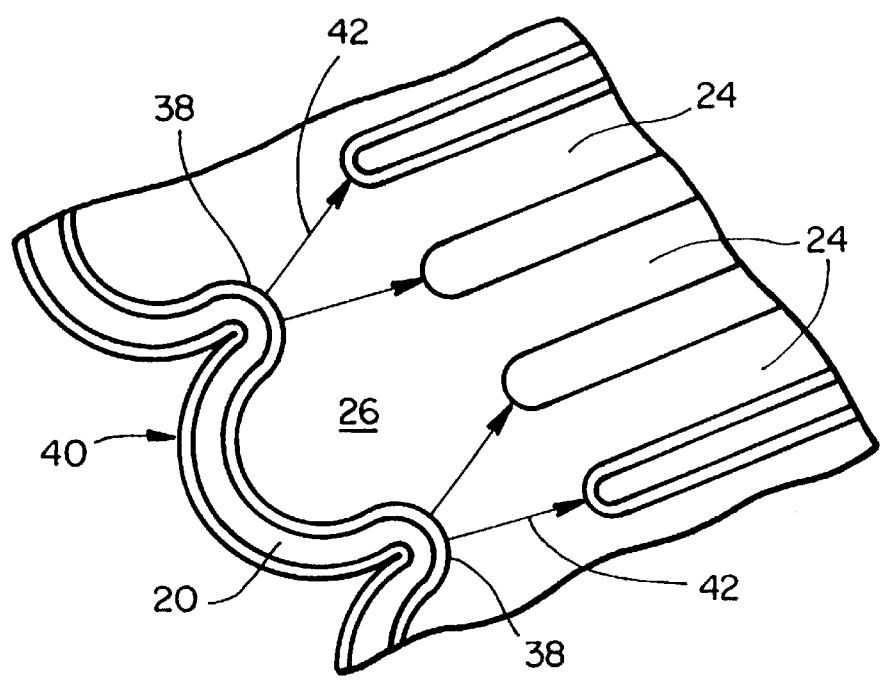
FIG_2
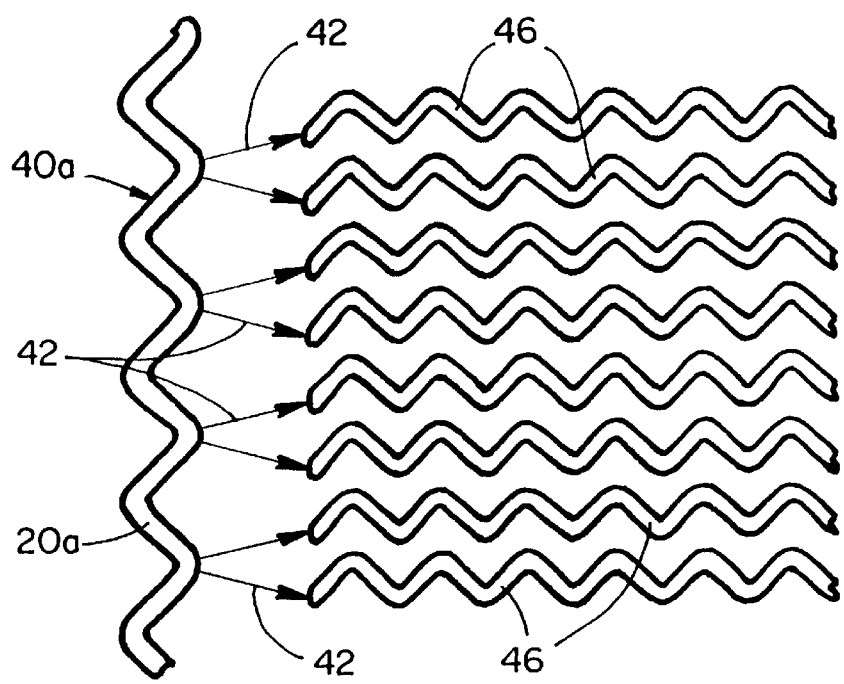
FIG_3

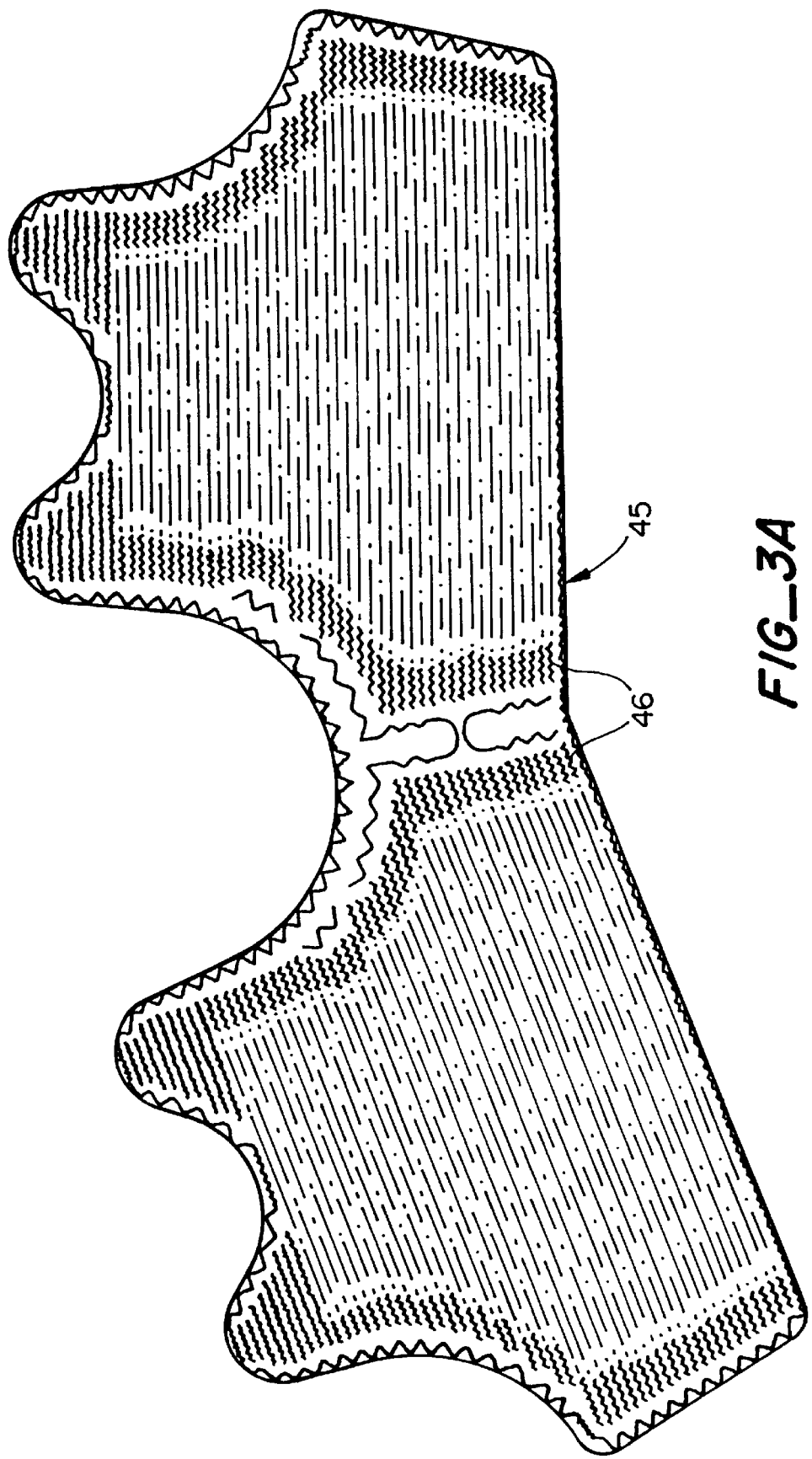
FIG_3A

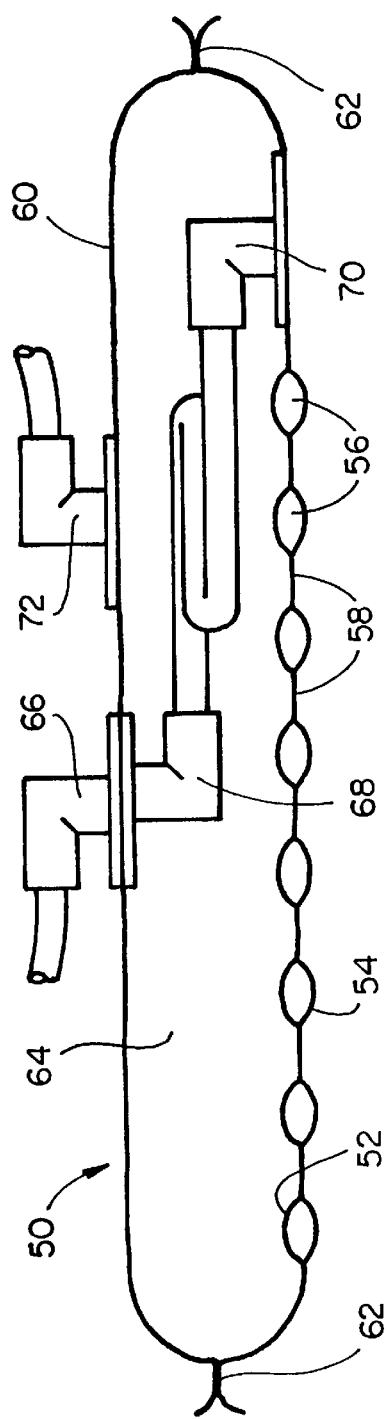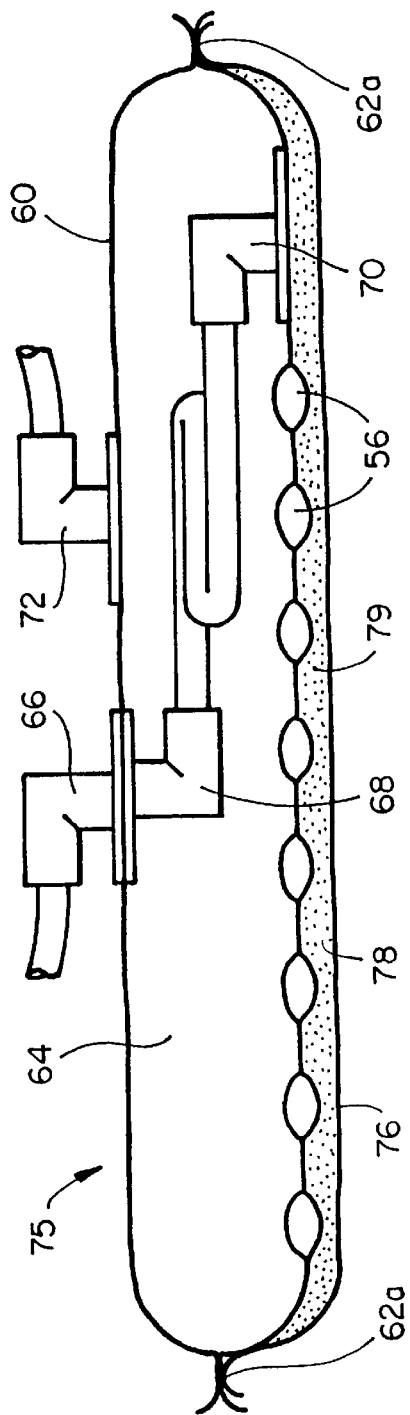
FIG_4  FIG_5

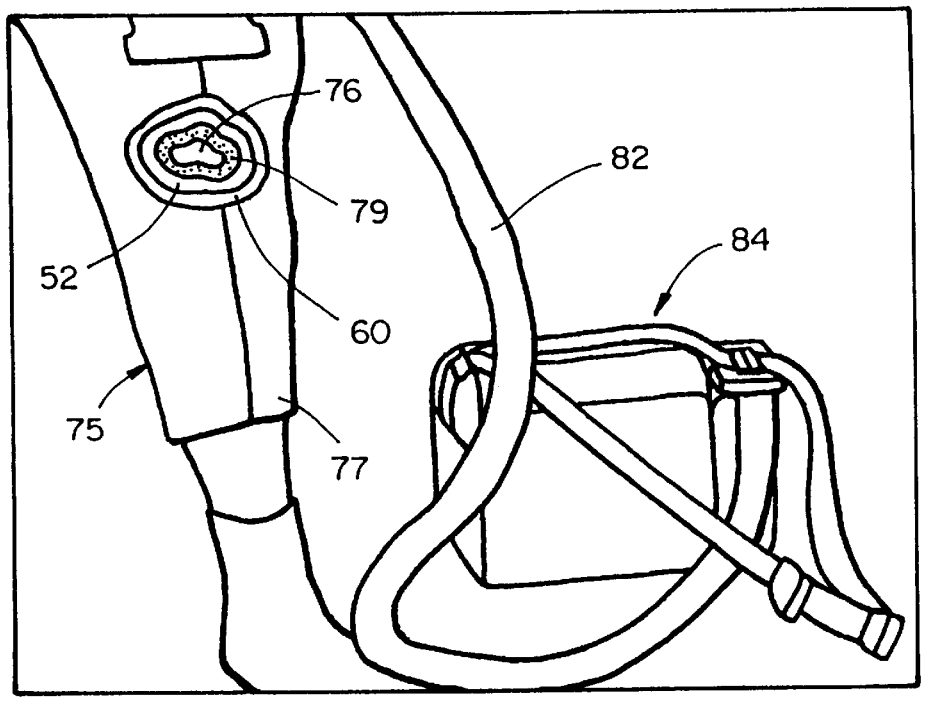
FIG_6
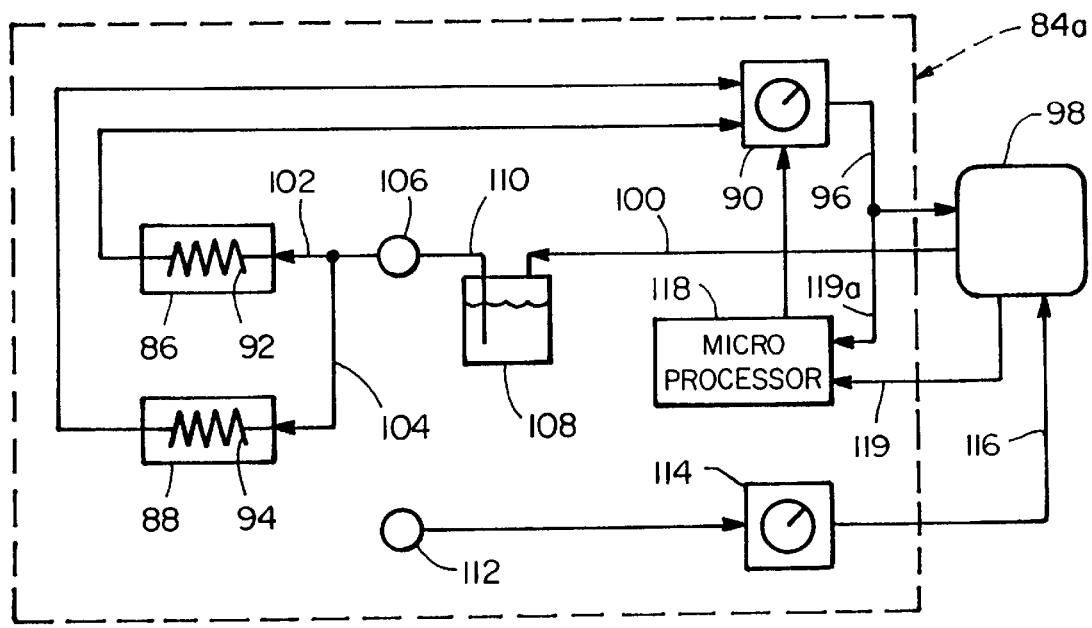
FIG_7

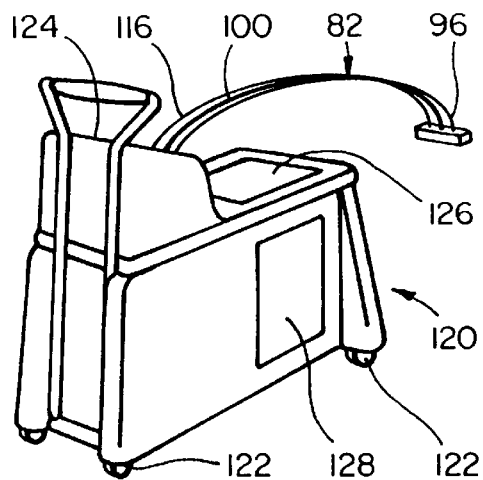
FIG_8
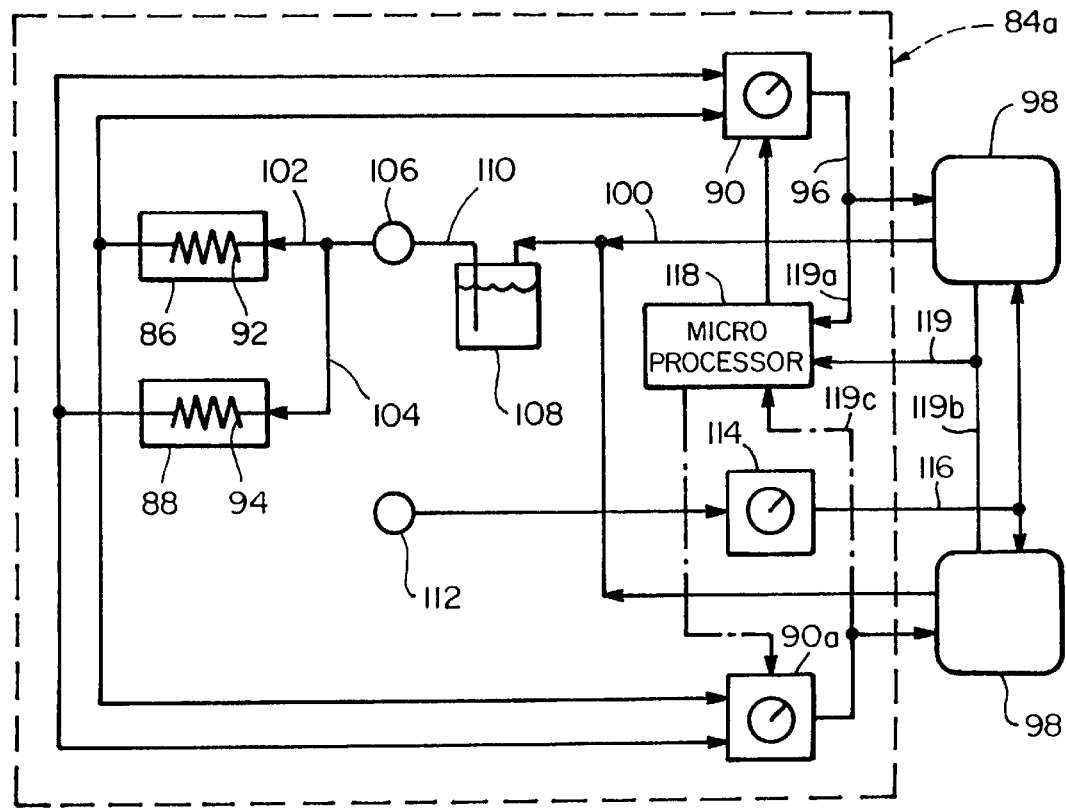
FIG_9

COOLING/HEATING SYSTEM

REFERENCE TO RELATED APPLICATION

This application is a continuation of application Ser. No 07/899,220, filed Jun. 16, 1992, now abandoned, which was a continuation of application Ser. No. 07/733,453, filed Jul. 22, 1991, now abandoned a continuation-in-part of application Ser. No. 07/431,753, filed Nov. 6, 1989, now U.S. Pat. No. 5,033,136, which was a division of application Ser. No. 07/250,778, filed Sep. 28, 1988, now U.S. Pat. No. 4,884,304.

BACKGROUND OF THE INVENTION

The invention relates generally to heat exchange devices for heating and/or cooling of the human body, and more particularly to a patient therapy heat exchange structure for placing against or for being worn on the human body. The heat exchange structure can be in combination with a cooperating portable device, which may be in the form of a wheeled cart, for providing heating and/or cooling liquid to the patient therapy device at a desired temperature, with or without cyclic pressurization.

U.S. Pat. No. 4,691,762 discloses a temperature control system including a heat exchanger vest and/or helmet to be worn on the human body, accompanied by a portable unit which administers cooling to a circulated liquid which passes through the heat exchange garments. The heat exchange garments pursuant to that patent were advantageously formed as Flexitherm (a trademark of Life Support Systems, Inc.), a material, fabricated of two sheets of flexible, liquid-impervious plastic material heat sealed together to form the fluid conducting channels with appropriate manifolding.

The Flexitherm heat exchange material as constituted prior to this invention had a tendency to exhibit flow constriction problems under certain circumstances. For example, in areas where the heat exchange material was subjected to relatively sharp bends, crease lines could form in the manifolds and in the fluid conducting channels themselves due to the stresses of bending the material when pressurized with flowing liquid. These stress lines or crease lines could become deep creases and shut off flow to some flow channels and through some portions of the manifolds. The problem was accentuated further by the imbalance in pressurization shrinkage between the flow channels and the manifolds. The flow channels shrink in lateral dimension when pressurized with liquid, since the flattened channels become "inflated" to a generally cylindrical configuration, drawing the structure inward laterally. Adjacent manifolds, which are generally perpendicular to the orientation of the flow channels, shrink in the perpendicular direction, but essentially do not shrink in the direction of shrinkage of the flow channels. Upon pressurization this imbalance tended to put increased stress on the manifolds, tending to form constrictions which were even more greatly accentuated when the Flexitherm heat exchange structure was formed around curves and bends on the body.

These problems limited the usefulness of the Flexitherm material for additional therapy situations which might require relatively sharp bends and flexing situations.

Co-pending application Serial No. 431,753, which was a division of application Ser. No. 250,778 (U.S. Pat. No. 4,884,304), disclosed a bedding system with liquid heating or cooling, wherein the liquid temperature control was provided by a mixing device which mixed warm liquid with cooled liquid as selected by the user, for maximum comfort. This provided for fast-response adjustment of temperature (and individual control in a dual control system) in the liquid flow channels of the bedding system, to quickly achieve the proper temperature for the particular user.

Such closed-loop mixing of heated and cooled liquids, to quickly achieve changes in temperature in a liquid-conducting flexible heat exchange device, was not generally available prior to the present invention. Conventional systems which have been in use have had only a single liquid tank, with the requirement of changing the temperature of water in the tank in order to achieve a change in temperature in a heat exchange device served by the tank. For example, heating/cooling devices of this general type have been available from Zero Cincinnati, Baxter Medical and Jobst.

It is an object of the present invention to provide an improved flexible heat exchange structure which may be used for thermal therapy on a patient or for other body cooling purposes, and this may be in conjunction with a portable source of heated and/or cooled liquid, and optionally air pressure, connected to the heat exchange structure or garment by fluid lines, for achieving very fast response in temperature adjustment for the patient thermal therapy.

SUMMARY OF THE INVENTION

In accordance with one embodiment of the invention, a flexible heat exchange structure, which may be used for heating and/or cooling of the human body, particularly for medical purposes but also for body thermal control in extreme environments, has a plurality of fluid conducting channels for carrying a heat exchange liquid. The channels are formed between a pair of flexible sheets of material, substantially impervious to the heat exchange liquid, with the sheets sealed together along generally parallel lines to form the liquid conducting channels between the lines. At the ends of the series of liquid conducting channels are manifolds for conducting the heat transfer liquid into the series of channels and out of the series of channels.

The pair of flexible sheets are sealed together around the series of liquid conducting channels along peripheral seal lines, spaced away from the ends of the channels in manifold portions so as to define the manifolds for inflow and outflow of liquid. In accordance with the invention the manifold portions of the seal lines have portions formed in a convoluted or undulating pattern. This pattern tends to discourage pinching of the fluid manifolds when the flexible heat exchange structure is subjected to bending or flexure as when worn on the human body. Further, the convoluted or undulating manifold seal lines tend to reduce buckling stress in the manifolds on pressurization of the heat exchange structure, by balancing pressurization shrinkage at the manifold portions of the seal lines with pressurization shrinkage laterally among the liquid conducting channels.

The sheets of flexible material preferably are heat sealed to form the seal lines, with the heat seals in a preferred embodiment being approximately 0.1" wide. Between the heat seal lines the fluid conducting channels may be approximately 0.15" wide when in flattened configuration. The convolutions in the manifold seal lines may have a width of about 0.5', forming a relationship discussed further below.

The convoluted or undulating pattern of seal lines can comprise a pattern of generally curved undulations, the undulations each having a width which is selected to shrink, upon pressurization of the heat exchange structure with fluid, to the same degree that the liquid conducting channels on the other side of the manifold shrink in width. This avoids the differential pressurization shrinkage mentioned above.

The undulations may be generally semi-circular in shape, or U-shaped, or they may V-shaped, with the open side of the U or V shape facing toward the series of liquid conducting channels on the other side of the manifold. In a preferred embodiment the apices of the generally curved undulations ("generally curved" includes V-shaped undulations), are positioned to be oriented generally toward the center of the open end of every second flow channel on the other side of the manifold, and generally equidistant from the two heat seal ends of the respective flow channels.

In a further preferred embodiment, the flow channels or capillaries of the heat exchange structure, while still being generally linear in an overall sense, are formed by seal lines in zig-zag patterns, the seal lines being regular repeating zig-zag lines generally equally spaced apart to form the liquid conducting channels between them. This zig-zag pattern of the channels tends to discourage pinching of the channels when the flexible heat exchange structure is subjected to bending or flexure, particularly around relatively tight bends or curves, as when worn on the human body.

In a further implementation of the invention a third flexible sheet of material is secured to the two-ply material, connected by sealed connection to one side of the fluid channel structure. This forms an air envelope between one of the pair of flexible sheets and the third sheet. Pressurized air can be received in this air envelope, to pressurize the heat exchange therapy device against the skin, such as on a human limb or torso, so that a combination of thermal therapy and pressure therapy can be applied to an injured area. The pressure also aids in conducting the heating or cooling into the skin, and it can be effective to control blood flow or swelling in the treated area.

In a still further implementation, a fourth sheet of flexible material is secured to the heat exchanger/fluid channel structure, on the opposite side from that of the air envelope. This forms a liquid or gel envelope within which a liquid or gel is contained, preferably permanently. The liquid or gel envelope disperses heating or cooling evenly against the patient's skin, especially when the air envelope is pressurized. This is important in critical hyperthermia or hypothermia treatment, where relatively extreme temperatures are involved and it is undesirable to have the thermal treatment applied in the discrete lines of the flow channels.

The apparatus of the invention further includes a portable device, which may be in the form of a wheeled cart, for administering the thermal therapy to a patient via the flexible heat exchange structure worn by the patient. Included in the portable device are two reservoirs, a heated liquid reservoir and a cooled liquid reservoir. A return reservoir, also for filling, preferably also is included. A mixing valve is provided to enable selection of precise temperature desired for the patient therapy, by adjusting the mixture of heated liquid and cooled liquid to be delivered to provide the correct temperature. Instantaneous changes may be made, as desired in certain types of patient therapy, by shifting of the mixture. Adjustments may be made anywhere from 100% cooled liquid to 100% heated liquid, by adjustment of the mixing valve.

Liquid which has passed through the patient therapy flexible heat exchange device via a pump reenters the portable apparatus into a return area. This return liquid is heated or cooled proportionally in accordance with the current setting of the mixing valve, as it re-enters the respective reservoirs. This provides for maximum efficiency of the portable device, and is advantageously achieved by providing closed, (substantially) full reservoirs which may have the chiller/heater unit inside the reservoir or in contact with the reservoir. The closed, non-vented reservoirs automatically receive the same return flow rate as the outgoing flow rate. Preferably a return reservoir, vented to atmosphere, first receives the return liquid, and the liquid is pumped from the return reservoir to the cooled and heated reservoirs in accordance with outflow from each reservoir.

Preferably the portable device also includes a source of pressurized air, i.e. a small compressor or pressurized air supply. This provides pressurized air for use in the air envelope discussed above, for administering pressure as well as hot/cold therapy to a patient.

It is therefore among the objects of the invention to provide improved apparatus and methods for administering cooling and/or heating to the human body, including a relatively constriction-free thermal flexible thermal therapy heat exchanger and a portable device for fast-response adjustment of hot/cold therapy. These and other objects, advantages and features of the invention will be apparent from the following description of preferred embodiments, considered along with the accompanying drawings.

DESCRIPTION OF THE DRAWINGS

FIG. 1 is a plan view showing a heat exchanger vest in flattened configuration, as one example of an improved construction of Flexitherm fluid heat exchange material.

FIG. 2 is a detail view showing a portion of the flexible heat exchange structure of FIG. 1.

FIG. 3 is a detailed plan view schematically showing a portion of a flexible heat exchange structure similar to that of FIG. 1, but including fluid flow channels formed in zig-zag patterns.

FIG. 3A is a plan view showing an entire heat exchange garment configured as shown in FIG. 3.

FIG. 4 is a view showing a three-ply or three-layer flexible heat exchange structure, similar to that of FIGS. 1 through 3 but including an additional layer of flexible material forming an air envelope for pressurization of the device during therapy.

FIG. 5 is a view similar to that of FIG. 4, but showing a four-ply or four-layer flexible heat exchange device, with the fourth layer forming a liquid or gel envelope to be placed against the patient, for more even distribution of heat or cooling from the heat exchanger channels.

FIG. 6 is a view in perspective showing the heat exchanger structure of FIG. 5 in use for patient therapy.

FIG. 7 is a schematic view showing a portable device, which may be in the form of a cart, for providing heated liquid, cooled liquid, selected mixtures of the liquids, and for providing air pressure for uses such as in FIG. 6.

FIG. 8 is a view in perspective showing the portable device of FIG. 7, in use with a flexible heat exchange therapy device, such as that of FIG. 4 or 5.

FIG. 9 is a view similar to FIG. 7, but showing a modified portable device capable of serving the treatment of several patients simultaneously, at different temperatures.

DESCRIPTION OF PREFERRED EMBODIMENTS

In the drawings, FIG. 1 shows a heat exchange garment 10 which is essentially of the type shown in FIG. 4 of U.S. Pat. No. 4,691,762, assigned to the same assignee as the present invention. The illustrated garment 10 is a vest for heating or cooling of the torso as shown, for example, in FIGS. 1A through 1F of the patent. The principles of the improved heat exchange garment 10 described herein are applicable to other garments or thermal therapy devices to be applied to the body, and to the temperature controlled bedding system disclosed in copending application Ser. No. 431,753 and U.S. Pat. No. 4,884,304.

As shown in FIG. 1, the heat exchange garment or thermal therapy device 10 is formed of a pair of sheets of flexible, liquid-impervious material (one side or layer 12 is visible in FIG. 1), sealed together along seal lines 14, 16, 18, 20, etc. As in the above referenced patent, the seal lines are preferably formed by heat sealing of layers of plastic material, as in the two-ply material known as Flexitherm. Thus, the sheets of material may comprise nylon, nonex or wool fabric coated with urethane, vinyl or other impermeable thermo setting plasters, for example.

Thus, the seal lines 16, shown in FIG. 1 as being linear seal lines in this case (they can be non-linear), form parallel fluid conducting channels 24 which act as fluid flow capillaries of the flexible heat exchange device 10. A peripheral seal line 14 forms the outermost capillary 24, while other peripheral seal lines 18, 20, 22 form manifolds for inflow and outflow of liquid to and from the capillaries or fluid conducting channels 24. Thus, as shown in the drawing, manifolds or manifold portions 26, 28, 30, 32, 34 and 36 are formed at the periphery of the garment or thermal therapy heat exchange device 10 in the configuration shown.

A principal feature of the present invention is that the primary manifolds of the flexible heat exchange device are configured to shrink with pressurization in such a way as to balance the pressurization shrinkage exhibited by the capillaries or flow channels 24. The heat exchange device 10 is formed flat, of two flat sheets sealed together. Typically a panel of the heat exchange material might have channel widths of 0.15 inch, with a 0.10 inch heat seal width. Upon pressurization with liquid, the capillaries or channels expand to a generally cylindrical shape, so that each channel has an approximate circumference of 0.30 inch. Assuming the cylindrical shape, the channel would then have a pressurized diameter of about 0.095 inch, as compared to the original flat width of 0.15 inch. Considering each channel and an adjacent heat seal width, the amount of shrinkage is 0.25 inch (flat) less 0.195 inch (pressurized), so that the foreshortening of the heat exchange device, laterally across the channels, shrinks the pressurized panel to about 0.195/0.25, or 78% of the flat panel dimension.

In prior flexible heat exchange devices of this nature, such as illustrated in U.S. Pat. No. 4,691,762, this lateral shrinkage was not balanced by a corresponding shrinkage in the fluid inlet and outlet manifolds. However, in accordance with the present invention the manifold seal lines (18, 20) are formed in an undulating or convoluted or zig-zag pattern. FIG. 1 shows one preferred embodiment wherein the convolutions are generally C-shaped, with apices 38 formed at connecting points. As illustrated in FIG. 1 and more particularly in FIG. 2, the heat seals 20 may form a double width at the point of the apex 38.

For best results in avoidance of stress, folding and crimping lines which can tend to pinch off the manifolds, it is preferred that the apices of each convolution or undulation are oriented at every second flow channel 24 on the other side of the fluid manifold 26, 30 or 36. This has been found to be most advantageous in avoiding extreme creasing in pressurization and in the bending or flexing of the heat exchange device around relatively sharp bends, such as when used to wrap a limb for thermal therapy on a patient.

The convolutions or undulations 40 cause the manifolds to shrink on pressurization, and these convolutions are shaped and sized so as to approximately balance the shrinkage which occurs laterally among the fluid flow channels 24. This eliminates most of the stress which would cause pinching or constriction of the fluid manifolds, an effect which is accentuated when the heat exchange garment is wrapped around tight bends.

Through working with the improved thermal therapy heat exchange device such as shown in FIGS. 1 and 2, it has been found that minimal stress lines occur on pressurization, usually a minor stress line forming along the lines 42 indicated in FIG. 2, extending between a convolution apex and approximately the end of the heat sealed lines adjacent to the facing flow channel. Little or no flow constriction is caused when the material is unflexed. When the material is wrapped laterally around a limb, for example, for thermal therapy of a patient, with the lines of the flow channels being wrapped circumferentially around the limb, a slight creasing or folding tends to occur at the back of the manifold 26, i.e. the layer of material which is closest to the skin. The outer layer then becomes taut, exhibiting virtually no creasing, and the manifold becomes only slightly constricted, well within a tolerance which continues to provide adequate flow through the flexible heat exchange device.

An example of preferred dimensions of a flexible heat exchange device in accordance with the invention is outlined below, showing the balancing of pressurization shrinkage at the manifold and at the capillaries. In this example the convolutions are c-shaped or v-shaped (zig-zag) and are 0.5 inch on centers. All heat seal widths are 0.10 inch. The capillaries or fluid flow channels are 0.15 inch wide when flat, between adjacent heat seals.

| | | |
|---|---|---|
| A. Nominal Heat Seal Width | = | 0.10" |
| B. Nominal Channel Width | = | 0.15" |
| C. Channel Circumference | = | 2 (0.15") = 0.30" |
| D. Channel Diameter | = | .3"/$\pi$ = 0.09549" |
| E. Ratio of Inflated Dimension to Flat Dimension | = | (.1" + 0.09549")/.25" = 0.782 |
| F. Manifold "V" or "C" | = | 0.5" (on center, flattened) |
| G. Nominal Heat Seal Width | = | 0.10" |
| H. Maximum Manifold Width | = | 0.5" – 2 (0.10") = 0.30" |
| I. Manifold "V" or "C" Diameter | = | 2 (0.30")/$\pi$ = 0.191" |
| J. Ratio of Inflated Dimension to Flat Dimension | = | 0.191" + 0.2"/0.5" = 0.782 |

As shown in FIG. 1, with the type of vest garment illustrated, the angle of the manifolds with the generally horizontally extending flow channels or capillaries 24 will vary depending on location. Thus, the convolutions or undulations in areas where the manifold is deeply angled away from perpendicular to the flow channels will need to be wider apart between the apices in order to maintain a relationship of orientation toward the end of every second flow channel. This will cause the pressurization shrinkage relationship to vary slightly, but not enough to appreciably inhibit flow through the manifolds, even when the flexible heat exchange device is wrapped around a limb or torso. In the manifold areas 28, 32 and 34 shown in FIG. 1, for example, the manifold is at an angle of less than about 45° to the flow channels. In this situation the differential shrinkage problem is minimized or avoided, without the typical undulations, by the fact that the manifolds are closer to alignment with the flow channels, which do not exhibit pressurization shrinkage in the longitudinal direction.

FIG. 3 schematically indicates a modified embodiment of the flexible heat exchange device of the invention. The convoluted or undulating manifold seal line 20*a* is shown as a zig-zag seal line, i.e. made up of V-shaped convolutions rather than U-shaped convolutions as in FIGS. 1 and 2. It should be understood that this configuration can be used in lieu of the U-shaped convolution pattern shown in FIG. 1, and in fact FIG. 1 shows a portion of a return manifold baffle 44 having the zig-zag or V-shaped configuration.

The principal difference of the embodiment shown in FIG. 3 is the zig-zag configuration of the capillary or flow channel seal lines 46. These seal lines 46 are formed as regular repeating zig-zag lines which remain essentially equidistant from each other and in conforming patterns, as illustrated in FIG. 3. The arrows in FIG. 3 represent stress lines which tend to be formed, extending from the apices of the zig-zag or semi-circular U-shaped manifold convolutions to the ends of seal lines at the channels across the manifold. As the improved flexible heat exchange structure of FIG. 3 is bent and flexed as in thermal therapy on a patient, it is observed that the stress lines are accentuated at the inside of the bend (e.g. the layer of material closest to the skin), while becoming less apparent or entirely disappearing on the outside layer of material at the same bend. For every apex in the manifold, two stress lines are formed to the facing ends of the heat seal lines defining the capillary channel. Thus, the stress of each line is one-half that of the previously known Flexitherm, referred to above. This results in at least a two time reduction in bending radius without occlusion of flow. This bending characteristic makes the new material far more compliant, enabling relatively sharp flexing of the material without occluding the flow of liquid either through the manifold or the channels.

FIG. 3A shows a full thermal vest 45 which is configured with the zig-zag flow channel heat seal lines. Manifold seal lines include zig-zag portions or V-shaped portions and U-shaped portions.

FIG. 4 is a schematic view in cross section, showing a three ply or three layer flexible heat transfer structure 50 in accordance with the invention. The flexible heat transfer device 50 is similar to that shown in FIGS. 1, 2 and 3, and may incorporate the configurations illustrated in those figures, in respect of two layers 52 and 54 which form liquid flow channels or capillaries 56, with seal lines 58 between them. In the heat exchange structure 50 of FIG. 4, an additional layer or ply 60 is included, on the outside of the heat exchange device, i.e. the side away from that which will engage a patient when the device is used for thermal therapy. The outer ply or layer 60, which is sealed to the other layers at peripheral seal lines 62, forms an air envelope 64 capable of containing pressure. This enables the heat exchange device 50, when wrapped around or against a patient's limb, torso, etc., to be pressurized to apply pressure against the treatment area. For example, one p.s.i.g. or slightly higher pressures are sufficient to effect certain types of pressure therapy while also administering heating and/or cooling therapy through the liquid conducting channels 56.

FIG. 4 schematically indicates liquid loop elbow fittings 66, 68 and 70 passing through the air containment layer 60 and through the outer liquid containment layer 52 in sealed relationship for conducting liquid into or out of the liquid flow channels 56. These fittings are repeated elsewhere to complete the inlet/outlet liquid loop. FIG. 4 also shows an air pressurization elbow fitting 72 for receiving pressurized air when the air containment envelope 64 is to be pressurized.

FIG. 5 is another schematic view in elevational cross section of a heat exchange structure 75 which is similar to that described in FIG. 4 but with a further layer or ply 76 secured to the liquid conducting channel structure at peripheral seal lines 62*a*. This lower ply or fourth ply is attached to the liquid conducting structure at the opposite side from the location of the air containment layer or ply 60 and the air envelope 64. The lower or fourth ply 76 forms a heat dispersing envelope 78 which contains a thermally conductive liquid or gel 79, preferably sealed into the envelope 78 permanently. When heated or cooled liquid flows through the liquid conducting flow channels 56, this liquid or gel envelope 78 assures that the heat or cooling will not be limited to specific lines of application, but will be dispersed properly against the skin of the patient. This is particularly critical in hyperthermia treatment for cancer, where fairly high temperatures (e.g. 106° to 108° F.) are involved. The pressurization of the air pressure chamber 64, with the four ply structure 75 wrapped around a treatment area and pressed against the skin via the pressure, would otherwise tend to apply the high heat along specific lines at the location of the liquid channels 56.

The structure and function of the four ply thermal/pressure therapy device 75 is otherwise similar to that described above relative to the three-ply structure 50.

FIG. 6 illustrates the four ply thermal/pressure therapy device 75 in use on a patient, in this case showing therapy applied to the knee and surrounding areas of the leg. The heat exchange structure 75 includes the air pressurization envelope and containment layer 60 just below a restraint layer 77 which holds the therapy device in place on the patient. The restraint layer 77 wraps around the leg or torso, retaining the thermal/pressure therapy device 75 against the leg or torso. It may be retained in position with Velcro hook and loop fasteners. The drawing is cut away to show the two-ply liquid channel structure (layer 52 is visible). Below the two-ply channel structure is the liquid or gel material 79 (see FIG. 5) and the bottom flexible layer 76. FIG. 6 can be considered to also illustrate the device 50 of FIG. 4, which also has the air pressurization envelope but not the liquid or gel envelope 78.

As shown in FIG. 6, a supply line or "umbilical cord" 82, which may be covered with fabric or other insulative material, feeds heat exchange liquid to and from the device 75 for heat exchange via the liquid conducting channels, and also includes and air line for feeding pressurized air into the air envelope 60. At the other end of this supply 82 is a heating, cooling and compressed air unit 84.

FIG. 7 is a schematic diagram illustrating the principal operative components of a portable unit such as the unit 84 shown in FIG. 6. The unit 84*a* illustrated in FIG. 7 may be in the form of a wheeled cart such as shown in FIG. 8, discussed further below.

As indicated in FIG. 7, the heat/cold/pressure supply unit 84*a* has a cooled liquid reservoir 86, a heated liquid reservoir 88, and a temperature control unit 90. In preferred embodiments, refrigeration or cooling coils 92 are directly in the liquid reservoir 86, and heating coils 94 are located directly in the liquid reservoir 88. These reservoirs preferably are closed and sealed, with a constant balance between liquid flowing out and liquid returning, as to each reservoir.

Liquid is delivered at a temperature selected via the temperature control unit 90 which mixes heated and cooled liquid to achieve the proper temperature in an outlet line 96. This liquid is delivered to the thermal therapy device 98 which is in contact with the patient, and which may be similar to the heat exchange garment 10 shown in FIG. 1 or 3, the three ply heat exchange/pressure device 50 shown in FIG. 4, or the four ply heat exchange/pressure unit 75 shown in FIG. 5. In any event, the liquid at selected temperature passes through capillaries of the thermal therapy device 98 and returns to a return area through a return line 100, ultimately to the cool and hot liquid tanks 86 and 88. The return line 100 could go directly to branch lines 102 and 104 leading to the cooled and heated liquid tanks if desired, provided some resilient expansion or accumulating capability is provided in the tanks 86 and 88 to allow for changes in volume of the closed loop system. This is necessary, for example, if a dry thermal therapy device 98 is connected to the system 84a, absorbing some of the liquid therein. In the arrangement just described, the liquid pump shown at 106 would be located in the line 96 so as to assure that positive pressure exists in the thermal therapy garment device 98.

However, a more preferred system is indicated in FIG. 7, including a return reservoir 108 receiving liquid from the liquid return line 100, and preferably vented to atmosphere (but alternatively sealed and expandable). Flexibility in the total volume of the system can thus be accommodated with the reservoir 108. The liquid pump 106 is then located just downstream of the return reservoir 108, delivering liquid at positive pressure to the cooled reservoir 86 or the warm reservoir 88 in the same proportion as liquid is being delivered from these respective reservoirs via the temperature control unit/mixing valve 90. Thus, the two reservoirs 86 and 88 can be rigid, closed and virtually completely filled at all times, and the positive pressure of the liquid pump 106 will push liquid from the reservoirs 86 and 88 in the desired proportion as set by the mixing valve 90 into the thermal therapy device 98. There is no draw on the return line 100, and negative pressure exists nowhere in this closed loop system except in a line 110 at the suction side of the pump, drawing liquid from the return reservoir 108.

As shown in FIG. 7, the portable unit 84a also preferably includes an air pump or air compressor 112, which delivers pressurized air via an air pressure control unit 114 and a delivery line 116 to the thermal/pressure therapy unit 98, which may be of the type shown in FIGS. 4 and 5, having a pressurized air envelope.

The liquid mixing valve 90, feeding hot and cold liquids mixed as selected to the thermal therapy device 98, is an important feature of the invention. As noted above, this arrangement allows nearly instantaneous changes in the temperature of therapy administered. In some types of therapy, for example in the treatment of sports injuries, there might be prescribed 48 hours of cooling therapy followed by alternate heating and cooling. The control system 84a indicated in FIG. 7 is very apt for this purpose.

Further, the temperature control device/mixing valve 90 can be connected to a microprocessor or programmed controller shown schematically at 118, or can contain such a microcontroller. This can enable the physician or therapist to preset timed sequential thermal changes as for the sports injury therapy noted above. Further, this can enable the most rapid approach possible to a target temperature, without overshooting the temperature. For example, in whole body hyperthermia for cancer treatment, relatively high temperatures are involved. In approaching a temperature of 108° F., for example, the controller might rapidly increase temperature at the thermal therapy unit 98 (which can be detected via a site temperature feedback line 119 or a feedback line 119a from the delivery line 96) to about 106°, then can increase the temperature on a slower basis, monitoring feedback through the line 119, until the precise desired temperature is reached. During the therapy, the desired temperature can be maintained in this same way, by feedback from the thermal heat exchange device 98, and control by the microcontroller 118. Electrically controlled valves, including solenoid operated valves, are available for this purpose.

In thermal therapy involving extreme temperatures, such as the whole body hyperthermia mentioned above, the temperature control enabled by the invention is extremely important. If in hyperthermia the body temperature rises to a dangerous point, which can cause heart fibrillation or brain damage, it is important to cool the patient very quickly. With conventional apparatus prior to this invention, it was necessary to quickly remove thermal covering from a patient and plunge the patient in a cold water or ice bath.

It should also be noted that several previous hyperthermia systems used a heavy rubbery blanket over the patient, which was somewhat insulative. A high temperature was used to achieve the desired temperature against the body, sometimes at 125°, far higher than the delivery temperature and higher than the skin burn temperature of about 113°. The present system delivers the desired temperature far more efficiently, without anywhere exceeding the skin burn temperature.

The thermal control system 84a shown in FIG. 7 automatically replenishes the hot and cold reservoirs 86 and 88 with the same amount of liquid being withdrawn, due to the fact of the reservoirs being closed. Whether a return liquid reservoir is included (vented to atmosphere or closed but expandable/contractible), the same desired effect can be achieved, as noted above.

FIG. 8 shows a cart 120 embodying the thermal/pressure supply unit 84a shown in FIG. 7. The portable device 120 preferably is in the form of a cart with wheels 122. Its size can be quite small, limited primarily by the volume of liquid (preferably water or treated water) which needs to be included in the cooling reservoir 86 and the heating reservoir 88. These volumes should be sufficient that a preselected temperature range can be maintained in each reservoir even though liquid may be returning to the two reservoirs at substantially different temperature from the reservoir temperature. Smaller volumes can be used in the reservoirs 86 and 88 provided the chilling element 92 and the heating element 94 have sufficient power to return the reservoirs quickly to the selected temperature range, or to maintain the exiting liquid at each reservoir at the desired range. As long as the desired temperature at the patient is not below that of the cold reservoir or above that of the hot reservoir, the desired therapy can be executed. The important consideration is that the system not be overloaded, such that the chilling and/or heating capacity is reduced below therapy requirements due to repeated turnover of mixed liquid back to the reservoirs. This of course depends on the size of the thermal therapy device(s) 98 and the difference between therapy temperature and body temperature for the particular therapy.

FIG. 8 shows a control panel 124 on the cart or portable device 120, for entering desired therapy parameters and for monitoring temperature at the patient therapy device 98, as discussed above. Details of the panel are not shown. A removable cover 126 can be provided in the top of the unit, primarily for access to the return liquid reservoir 108, which also serves as a fill reservoir for adding makeup liquid. On the side of the portable device 120 is shown another openable panel 128, for access to contained components.

The cord 82 is shown with several lines, including the liquid delivery line 96, the liquid return line 100 and the pressurized air line 116. Also included in this cord or bundle 82 is the thermocouple line 119 (or 119a—see FIG. 7) which feeds back the temperature of the thermal therapy device 98 to the controller.

FIG. 9 shows a modification of the system shown in FIG. 7, demonstrating that the same system can be used to serve two or more patient thermal therapy devices 98. A common cool liquid reservoir 86 and a common heated liquid reservoir 88 can serve cooled and heated liquid lines 130 and 132 leading to two different temperature control liquid mixing valves 90 and 90*a*, as shown. Temperature can thus be controlled individually to the respective thermal therapy units 98. The power and response time of the chiller 92 and the heater 94 should be sufficient to serve multiple thermal therapy devices 98 simultaneously.

The microprocessor 118 is shown serving both temperature control mixing valves 90, 90*a*. It can receive temperature feedback from thermocouple lines 119 or 119*a* (for the controller 90) and 119*b* or 119*c* (for the controller 90*a*).

The two therapy units 98 are shown receiving compressed air from the air pressure control unit 114. Pressure regulators (not shown) for individual control of pressure therapy can be included if desired. The microprocessor 118 is indicated as controlling the air pressure control unit 114.

The above described preferred embodiments are intended to illustrate the principles of the invention, but not to limit its scope. Other embodiments and variations to these preferred embodiments will be apparent to those skilled in the art and may be made without departing from the spirit and scope of the invention as defined in the following claims.

I claim:

1. A flexible heat exchange structure having a pair of superposed sheets of flexible material sealed together to form a plurality of fluid-conducting channels which tend to Inflate and decrease in width when a pressurized liquid passes through them, and a manifold in fluid communication with the channels at one end thereof which also tends to be inflated by the pressurized liquid, the manifold having an undulating wall which extends in a direction generally perpendicular to the channels and has apices which face the channels and are spaced apart by a distance that decreases to the same degree that the width of the channels decreases upon pressurization of the structure.

2. The heat exchange structure of claim 1 wherein the sheets are sealed together along continuous lines to form the channels.

3. The heat exchange structure of claim 1 wherein the channels are formed in a zig-zag pattern.

4. The heat exchange structure of claim 1 wherein adjacent ones of the apices are aligned with alternate ones of the channels.

5. The heat exchange structure of claim 1 further including a third sheet of flexible material overlying one of the superposed sheets to form an air chamber on one side of the structure.

6. The heat exchange structure of claim 1 further including a layer of heat dispersive material adjacent to one of the superposed sheets.

7. The heat exchange structure of claim 1 further including means communicating with the manifold for circulating liquid through the channels.

8. The heat exchange structure of claim 7 wherein the means for circulating liquid through the channels comprises a heated liquid reservoir, a cooled liquid reservoir, an adjustable mixing valve connected between the reservoirs and the manifold for mixing liquids from the two reservoirs in any desired proportion for delivery to the channels, and means for circulating the liquid through the two reservoirs, the mixing valve and the channels.

9. The heat exchange structure of claim 8 wherein the means for circulating the liquid through the two reservoirs, the mixing valve and the channels includes a return reservoir for receiving liquid which has circulated through the channels, and a pump connected between the return reservoir and the other two reservoirs for pumping liquid from the return reservoir through the heated liquid reservoir and the cooled liquid reservoir to the channels.

10. A flexible heat exchange structure having a pair of superposed sheets of flexible material sealed together to form a plurality of fluid-conducting channels which tend to inflate and decrease in width when a pressurized liquid passes through them, and a manifold in fluid communication with the channels at one end thereof which also tends to be inflated by the pressurized liquid, the manifold having an undulating wall which is oriented and dimensioned to decrease in dimension to the same degree that the width of the channels decreases upon pressurization of the structure.

11. The heat exchange structure of claim 10 wherein the undulating wall is formed by a series of generally semicircular seals connected together in an undulating pattern.

12. The heat exchange structure of claim 10 wherein the undulating wall is formed by a series of V-shaped seals connected together in a zig-zag pattern.

13. A heat exchange system for thermal treatment of a body, comprising a heat exchange panel having first and second superposed sheets of flexible material sealed together to form a plurality of fluid-conducting channels which tend to inflate and decrease in width when a pressurized liquid passes through them, and a manifold in fluid communication with the channels at one end thereof which also tends to be inflated by the pressurized liquid, the manifold having an undulating wall which is oriented and dimensioned to decrease in dimension to the same degree that the width of the channels decreases upon pressurization of the panel, an outer layer which is adapted to be wrapped about the body to hold the panel on the body with the first sheet facing the body, an air chamber between the outer layer and the second sheet, means for pressurizing the air chamber to urge the heat exchange panel against the body, and a heating/cooling unit for circulating liquid of predetermined temperature through the panel.

14. The system of claim 13 wherein the means for pressurizing the air chamber and the heating/cooling unit are combined in a separate unit and connected to the panel by flexible lines.

15. The system of claim 13 further including a hook and loop fastener attached to the outer layer for securing the device to the body.

16. The system of claim 13 further including a layer of heat dispersive material adjacent to the first sheet for providing more uniform heat transfer between the body and liquid in the channels.

17. A personal. heating/cooling system, comprising a heat exchange panel having a pair of superposed sheets of flexible material sealed together to form a plurality of fluid-conducting channels which tend to inflate and decrease in width when a pressurized liquid passes through them, and a manifold in fluid communication with the channels at one end thereof which also tends to be inflated by the pressurized liquid, the manifold having an undulating wall which is oriented and dimensioned to decrease in dimension to the same degree that the width of the channels decreases upon pressurization of the panel, a heated liquid reservoir, a cooled liquid reservoir, an adjustable mixing valve connected between the reservoirs and the panel for mixing liquids from the two reservoirs in any desired proportion for delivery to the panel, a return reservoir for receiving liquid from the panel, and a pump for pumping liquid from the return reservoir through the heated reservoir and the cooled reservoir to the flow channels.

18. The system of claim 17 wherein the pump is connected between the return reservoir and the other two reservoirs.

19. A flexible heat exchange structure having a pair of superposed sheets of flexible material sealed together in a plurality of spaced apart descrete areas to form a fluid-conducting channel which inflates and decreases in lateral dimension upon pressurization by a fluid, and means sealing the sheets together along an undulating line to form a chamber which communicates with the channel and also inflates and decreases in lateral dimension upon pressurization, the undulating line being oriented and dimensioned to make the decreases in lateral dimension substantially equal in the channel and in the chamber.

20. The heat exchange structure of claim 19 wherein the sheets are sealed together along continuous, generally parallel lines to form the channel.

* * * * *